(12) United States Patent
Swanson et al.

(10) Patent No.: US 8,759,008 B2
(45) Date of Patent: Jun. 24, 2014

(54) ROBUST, SELF-ASSEMBLED, BIOCOMPATIBLE FILMS

(75) Inventors: Basil I. Swanson, Los Alamos, NM (US); Aaron S. Anderson, Los Alamos, NM (US); Andrew M. Dattelbaum, Los Alamos, NM (US); Jurgen G. Schmidt, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 807 days.

(21) Appl. No.: 12/777,837

(22) Filed: May 11, 2010

(65) Prior Publication Data

US 2010/0267170 A1    Oct. 21, 2010

Related U.S. Application Data

(62) Division of application No. 11/788,183, filed on Apr. 18, 2007.

(60) Provisional application No. 60/793,195, filed on Apr. 18, 2006.

(51) Int. Cl.
*G01N 33/53*    (2006.01)

(52) U.S. Cl.
USPC .......................................................... 435/7.1

(58) Field of Classification Search
None
See application file for complete search history.

(56) References Cited

U.S. PATENT DOCUMENTS

| | | | |
|---|---|---|---|
| 5,403,928 A | 4/1995 | Arrhenuis | |
| 2002/0013003 A1* | 1/2002 | Wagner et al. | 436/518 |
| 2002/0106702 A1* | 8/2002 | Wagner et al. | 435/7.9 |
| 2005/0277119 A1* | 12/2005 | Dandliker et al. | 435/6 |

OTHER PUBLICATIONS

Zhu et al., Chemical vapor deposition of organic monolayers on Si(100) via Si-N linkages, 1999, Langmuir, 15: pp. 8147-8154.*
Lee et al., "Protein-resistant coatings for glass and metal oxide surfaces derived from oligo (ethylene glycol)-terminated alkyltrichlorosilanes," Biomaterials, 1998, vol. 19: pp. 1-7.
Meagher et al., "A very thin coating for capillary zone electrophoresis of proteins based on a tri(ethylene glycol)-terminated alkyltrichlorosilane," Electrophoresis, 2004, vol. 25, pp. 1-10.
Martinez et al., "Pathogen detection using single mode planar optical waveguides," Journal of Materials Chemistry, vol. 15, pp. 1-9, Sep. 23, 2005.
Pale-Grosdemange et al., "Formation of Self-Assembled Monolayers by Chemisorption of Derivatives of Oligo (ethylene glycol) of Structure HS (CH2) 11(OCH2CH2)mOH on Gold 1," J. Am. Chem. Soc., Jan. 1, 1991, vol. 113, pp. 12-20.

(Continued)

*Primary Examiner* — N. C. Yang
(74) *Attorney, Agent, or Firm* — Klarquist Sparkman, LLP

(57) ABSTRACT

The present invention provides a composite material including a substrate having an oxide surface, and, a continuous monolayer on the oxide surface, the monolayer including a silicon atom from a trifunctional alkyl/alkenyl/alkynyl silane group that attaches to the oxide surface, an alkyl/alkenyl/alkynyl portion of at least three carbon atoms, a polyalkylene glycol spacer group, and either a reactive site (e.g., a recognition ligand) or a site resistant to non-specific binding (e.g., a methoxy or the like) at the terminus of each modified SAM. The present invention further provides a sensor element, a sensor array and a method of sensing, each employing the composite material. Patterning is also provided together with backfilling to minimize non-specific binding.

18 Claims, 11 Drawing Sheets

(56) References Cited

OTHER PUBLICATIONS

Prime et al., "Adsorption of Proteins onto Surfaces Containing End-Attached Oligo(ethylene oxide) a Model System Using Self-Assembled Monolayers," J. Am. Chem. Soc, Nov. 1993, vol. 115, pp. 10714-10721.

Herrwerth et al., "Factors that Determine the Protein Resistance of Oligoether Self-Assembled Monolayers—Internal Hydrophilicity, Terminal Hydrophilicity, and Lateral Packing Density," J. Am. Chem. Soc., Jul. 15, 2003, vol. 125, pp. 9359-9366.

Kelly et al., "Integrated optical biosensor for detection of multivalent proteins," Optics Letters, Dec. 1, 1999, vol. 24, pp. 1723-1725.

Anderson et al., "Functional PEG-Modified Thin Films for Biological Detection," Langmuir, vol. 24 No. 5, pp. 2240-2247.

* cited by examiner

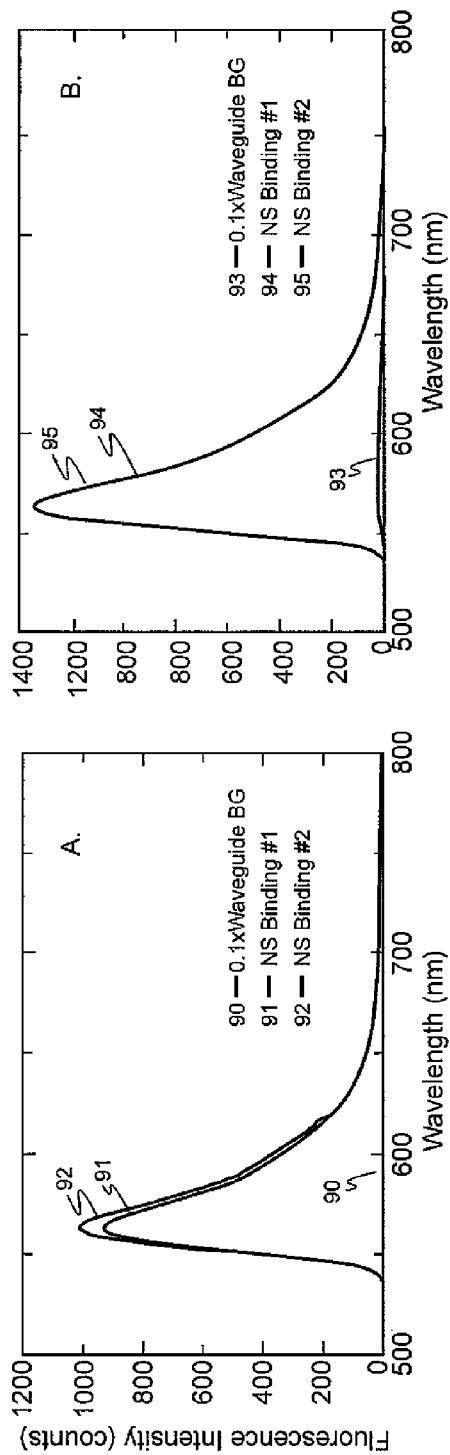
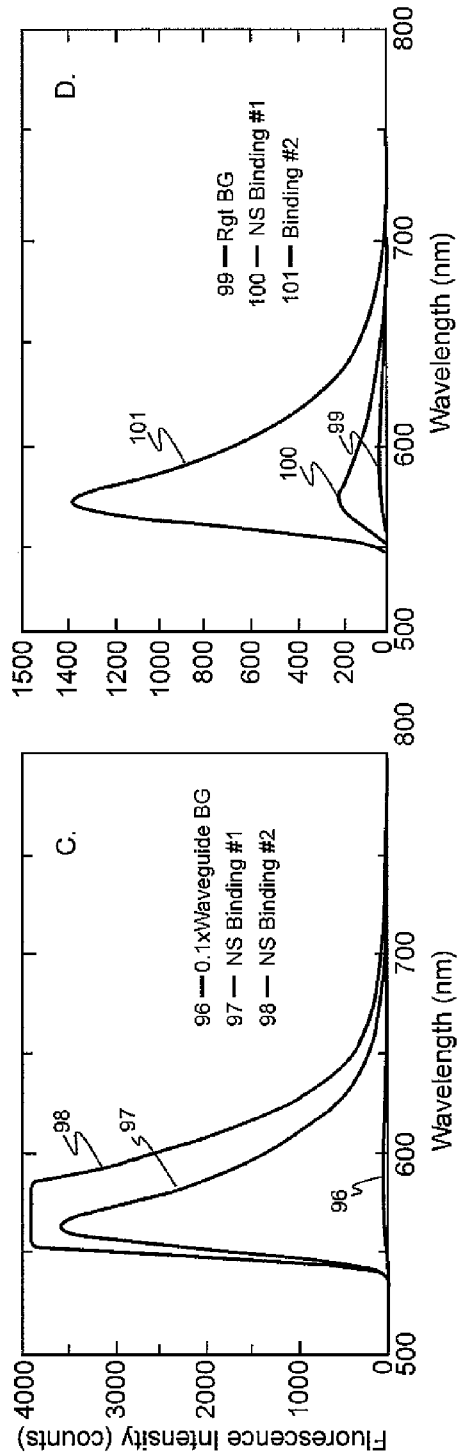
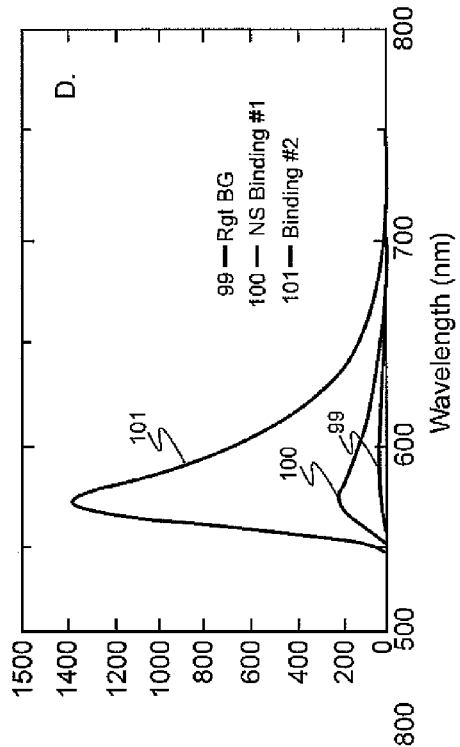
Fig. 11a, Fig. 11b, Fig. 11c, Fig. 11d

ROBUST, SELF-ASSEMBLED, BIOCOMPATIBLE FILMS

RELATED APPLICATIONS

This application is a divisional application of U.S. patent application Ser. No. 11/788,183, filed Apr. 18, 2007, which in turn claims the benefit of U.S. Provisional patent application 60/793,195, filed on Apr. 18, 2006.

STATEMENT REGARDING FEDERAL RIGHTS

This invention was made with government support under Contract No. DE-AC51-06NA25396 awarded by the U.S. Department of Energy. The government has certain rights in the invention.

FIELD OF THE INVENTION

The present invention relates generally to substrates including a coating of a self-assembled monolayer (SAM) upon the surface of the substrate. The present invention further relates to applications of such coated substrates including, e.g., use in sensing and use in environments subject to bio-fouling.

BACKGROUND OF THE INVENTION

Assays for the detection of target species such as cholera toxin and *Bacillus anthracis* protective antigen (PA) have been known using phospholipids bilayer membranes supported on a silica-coated waveguide platform (see, Martinez et al., J. Mat. Chem., vol. 15, pp. 4639-4647, (2005)). While lipid membranes offered excellent resistance to non-specific binding, lipid membranes are not robust and do not endure either prolonged storage or use under harsh conditions.

In the past, many groups have explored various PEGylated SAMs that have a short attachment group to the oxide surface with terminal polyethylene glycols (PEGs) of varying lengths. Often, the synthetic route to these earlier SAMs was through use of either a methyl-diethoxy-silane or a methyl-dimethoxy-silane. Although previous SAMs based on this approach showed good antifouling properties (non-specific binding) using optical microscopy, they did not exhibit good non-specific binding when using a waveguide-based sandwich assay approach. The reason for this difference is the relatively high optical intensity at the surface of the planar optical waveguide relative to the optical field intensity used in confocal microscopy. Essentially, the use of evanescent excitation is much more sensitive.

The failures of earlier diethoxy-methyl-aminopropylsilane-based SAMs in waveguide assays prompted reevaluation of surface chemistries. Whitesides and Grunze provide examples of PEG-terminated alkylthiols that are very good at resisting non-specific protein adsorption when analyzed by fluorescence microscopy (see Grosdemange et al., J. Am. Chem. Soc., vol. 113, pp. 13-20 (1993) and Herrwerth et al., J. Am. Chem. Soc., vol. 125, pp. 9359-9366 (1993)). The advantages of their films include dense packing due to the hydrophobic interactions of the alkyl chains, as well as the hydrophilicity of the terminal polyethylene glycol units. However, their films are prepared on metal surfaces, e.g., silver and gold. These films would not work for oxide surfaces like those used in the currently desired optical methods.

SUMMARY OF THE INVENTION

In accordance with the purposes of the present invention, as embodied and broadly described herein, the present invention includes a composite material including substrate having an oxide surface, and, a monolayer thereon the oxide surface, the monolayer including a first species of the formula $X-Q-Z_1$ where X includes a silicon atom from a trifunctional alkyl/alkenyl/alkynyl silane group for attachment to the oxide surface, Q represents a central portion of the trifunctional alkyl/alkenyl/alkynyl silane group and serves as a spacer group of an alkane, or a combination of an alkane and one or more of an alkene or an alkyne group having greater than about 3 carbons, the spacer group promoting self assembly of a plurality of the species, and $Z_1$ is a functional moiety that provides a site for attachment of a recognition ligand (R), and, a second species of the formula $X-Q-Z_2$ where X includes a silicon atom from a trifunctional alkyl/alkenyl/alkynyl silane group for attachment to the oxide surface, Q represents a central portion of the trifunctional alkyl/alkenyl/alkynyl silane group and serves as a spacer group of an alkane, or a combination of an alkane and one or more of an alkene or an alkyne group having greater than about 3 carbons, the spacer group promoting self assembly of a plurality of the species, $Z_2$ is a functional moiety that provides a site for attachment of a terminal moiety (T) that provides resistance to non-specific binding by the composite material.

The present invention further includes a sensor element for use in a system for detection of a target species, the element including a substrate having an oxide surface; and, a one or more recognition groups thereon wherein the one or more recognition groups are in a monolayer upon the oxide surface, the monolayer including a first species of the formula $X-Q-Z_1$ where X includes a silicon atom from a trifunctional alkyl/alkenyl/alkynyl silane group for attachment to the oxide surface, Q represents a central portion of the trifunctional alkyl/alkenyl/alkynyl silane group and serves as a spacer group of an alkane, or a combination of an alkane and one or more of an alkene or an alkyne group having greater than about 3 carbons, the spacer group promoting self assembly of a plurality of the species, and $Z_1$ is a functional moiety that provides a site for attachment of one or more recognition ligands (R), and, a second species of the formula $X-Q-Z_2$ where X includes a silicon atom from a trifunctional alkyl/alkenyl/alkynyl silane group for attachment to the oxide surface, Q represents a central portion of the trifunctional alkyl/alkenyl/alkynyl silane group and serves as a spacer group of an alkane, or a combination of an alkane and one or more of an alkene or an alkyne group having greater than about 3 carbons, the spacer group promoting self assembly of a plurality of the species, $Z_2$ is a functional moiety that provides a site for attachment of a terminal moiety (T) that provides resistance to non-specific binding upon the waveguide substrate.

The present invention still further includes a method of detecting a target species including contacting a sample including a potential target species with a sensor element including a substrate having an oxide surface and a monolayer upon the oxide surface, the monolayer including a first species of the formula $X-Q-Z_1$ where X includes a silicon atom from a trifunctional alkyl/alkenyl/alkynyl silane group for attachment to the oxide surface, Q represents a central portion of the trifunctional alkyl/alkenyl/alkynyl silane group and serves as a spacer group of an alkane, or a combination of an alkane and one or more of an alkene or an alkyne group having greater than about 3 carbons, the spacer group promoting self assembly of a plurality of the species, and $Z_1$ is a functional moiety that provides a site for attachment of a recognition ligand (R) adapted for binding to a pre-selected target species, and, a second species of the formula $X-Q-Z_2$ where X includes a silicon atom from a trifunctional alkyl/alkenyl/alkynyl silane group for attachment to the oxide surface, Q represents a central portion of the trifunctional alkyl/alkenyl/alkynyl silane group and serves as a spacer group of an alkane, or a combination of an alkane and one or more of an alkene or an alkyne group having greater than about 3 carbons, the spacer group promoting self assembly of a plurality of the species, $Z_2$ is a functional moiety that provides a site for attachment of a terminal moiety (T) that provides resistance to non-specific binding upon the sensor element; and, detecting a signal arising in response to binding between the recognition ligand and any targeted species.

The present invention still further sensor array on an oxide substrate, the array including a substrate having an oxide surface, a monolayer upon the oxide surface, the monolayer including discrete portions upon the oxide surface where a first species of the formula $X-Q-Z_1$ where X includes a silicon atom from a trifunctional alkyl/alkenyl/alkynyl silane group for attachment to the oxide surface, Q represents a central portion of the trifunctional alkyl/alkenyl/alkynyl silane group and serves as a spacer group of an alkane, or a combination of an alkane and one or more of an alkene or an alkyne group having greater than about 3 carbons, the spacer group promoting self assembly of a plurality of the species, and $Z_1$ is a functional moiety that provides a site for attachment of one or more recognition ligands (R) for one or more corresponding pre-selected target species, wherein each different recognition ligand for a corresponding pre-selected target species is located within a different discrete portion upon the oxide surface and, a second species of the formula $X-Q-Z_2$ where X includes a silicon atom from a trifunctional alkyl/alkenyl/alkynyl silane group for attachment to the oxide surface, Q represents a central portion of the trifunctional alkyl/alkenyl/alkynyl silane group and serves as a spacer group of an alkane, or a combination of an alkane and one or more of an alkene or an alkyne group having greater than about 3 carbons, the spacer group promoting self assembly of a plurality of the species, $Z_2$ is a functional moiety that provides a site for attachment of a terminal moiety (T) that provides resistance to non-specific binding, and, where the monolayer in areas other than the discrete portions upon the oxide surface include only the second species of the formula $X-Q-Z_2$.

BRIEF DESCRIPTION OF THE DRAWINGS

FIGS. 11(a), 11(b) and 11(c), show graphs of waveguide assays with the respective long-alkyl chain SAMs of PEG4-OCH3, PEG-OH, and PEG8-OCH3 while 11(d) shows a graph of a binding assay of the hybrid SAM shown in FIG. 9. The graphs show the various levels of non-specific binding with FIG. 11(d) showing a ratio of non-specific binding to background of 5.8 and ratio of specific binding to non-specific binding of 5.7, which is comparable to current membrane levels.

DETAILED DESCRIPTION

The present invention concerns composite materials having substrates with an oxide surface and a thin film monolayer upon the oxide surface that can be used in applications such as bio- or chemical-sensing, in drug delivery, or in providing a surface resistance to biofouling. The composite materials of the present invention can be stored for weeks in buffer solution without deleterious effects, can be stable in air for as long as two weeks or more, can undergo stringent rinsing conditions (e.g., with Tween-20) without loss of performance, can be reusable and can allow for certain flexibility in chemistry with respect to alkyl (or alternatively alkenyl or alkynyl) chain length, polyalkylene glycol length, passive or non-binding surface preparation, and selection of terminal functionality.

This is a materials invention that can be used in a variety of applications where stable, biocompatible films are needed. A chemical route to stable self-assembled monolayers that exhibit very low non-specific binding of biomolecules and organisms, and that can be used to conjugate other molecules of these materials has been developed. The SAMs are based on densely packed alkane-polyethylene glycol units self-assembled to oxide surfaces. Applications may include robust sensor surfaces, surface coatings to minimize bio-fouling, highly selective capturing particles (such as glass or magnetic beads) and optimized drug delivery using nanoparticles. The non-specific binding properties of these films generally compare favorably to those of lipid bilayer membranes, which are nature's way of minimizing non-specific interactions of cells and biomolecules. The increased stability of these SAMs over membranes will allow the generation of reusable surfaces.

Figure 2:
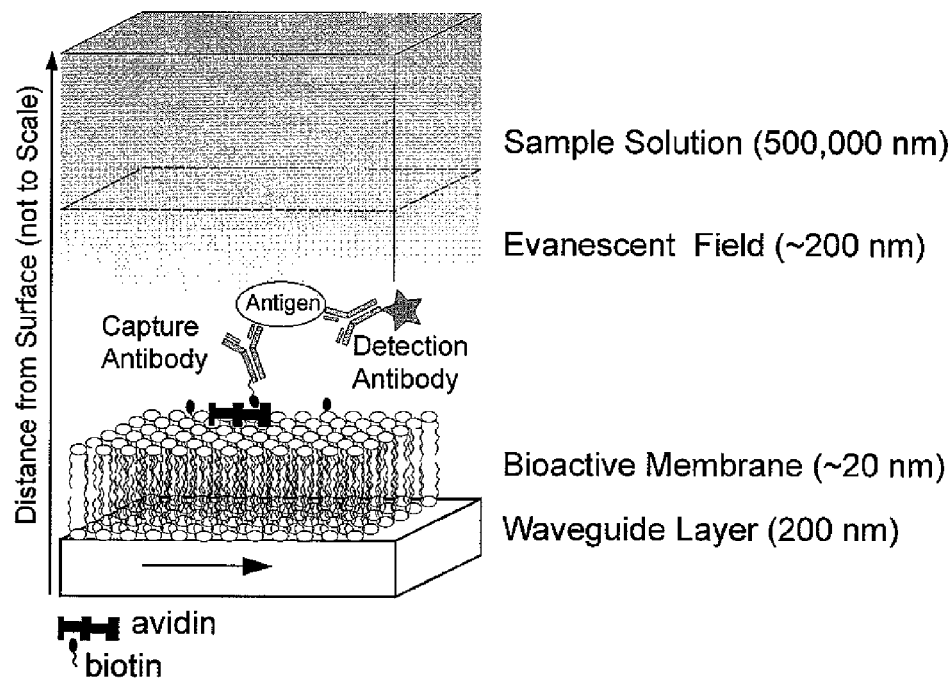
FIG. 2 illustrates a schematic drawing of a sandwich assay on a membrane surface. In accordance with the present invention, the membranes are replaced with the synthetically developed, covalently attached self-assembled membrane (SAM), i.e., a PEG-based SAM.
Figure 3:
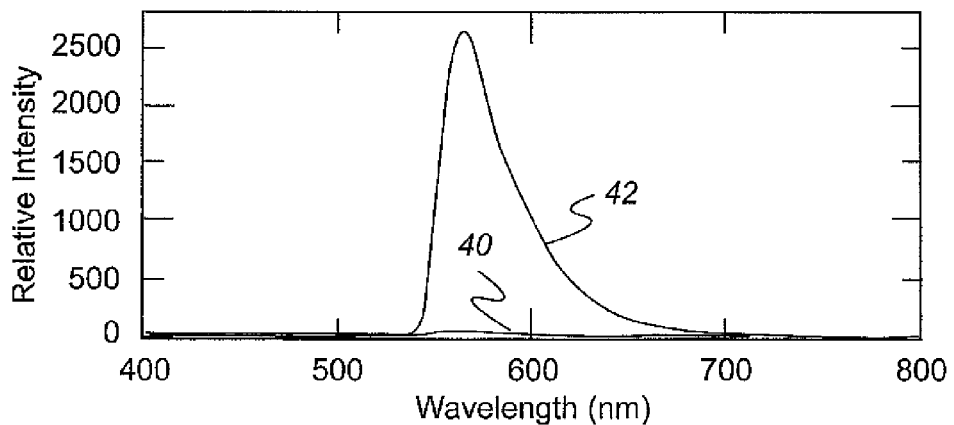
FIG. 3 illustrates a graph showing the emission spectra of protective antigen (PA) sandwich assay using a membrane surface, where both the non-specific binding and desired binding are shown.
Figure 4:
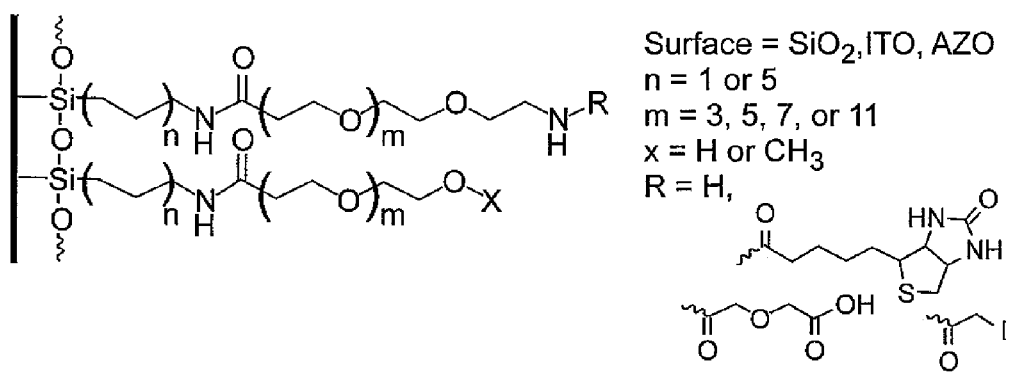
FIG. 4 shows a synthetic scheme for preparation of the SAMs used in accordance with the present invention.
Figure 5:
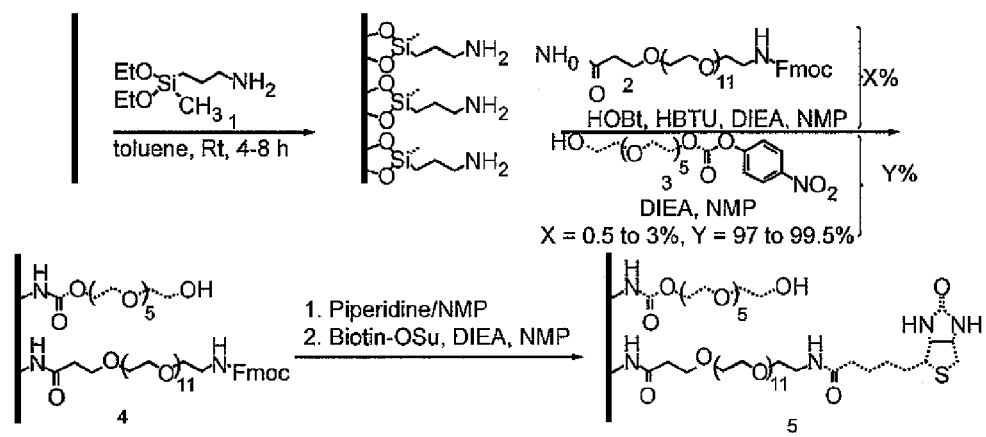
FIG. 5 shows a synthetic scheme for preparation of the short-alkyl chain SAMs, such SAMs serving as a comparison to the materials of the present invention.
Figure 6:
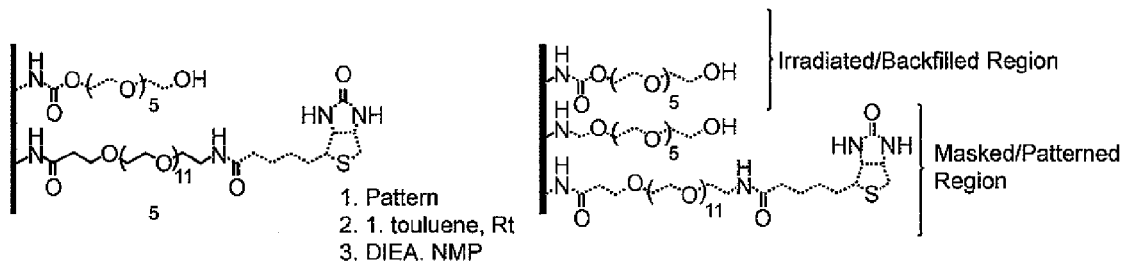
FIG. 6 illustrates a patterning approach to SAMs, such a patterning process useful in accordance with the present invention.
Figure 7B:
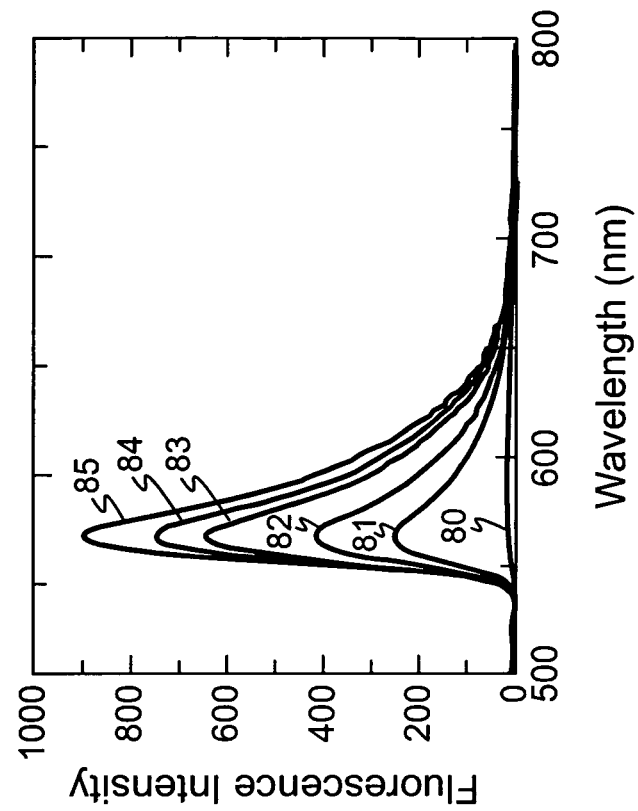
FIGS. 7(a) and 7(b) show plots of waveguide experiments demonstrating the problem presented by non-specific binding, such binding being reduced by the SAMs developed in the present invention.
Figure 7A:
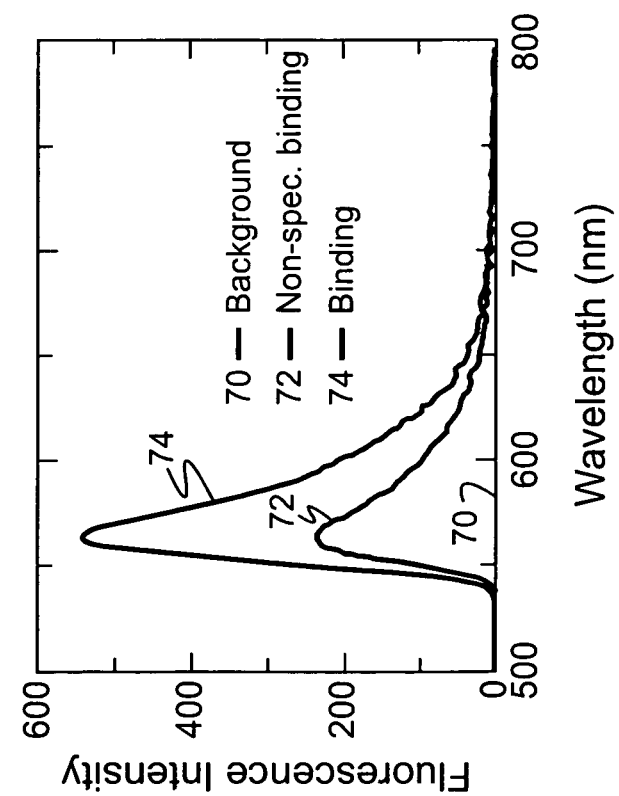

The self-assembled monolayers used in accordance with the present invention are based on tightly packed SAMs terminated with polyethylene glycol (PEG) units with an occasional reactive group for conjugation to an effector group (e.g., a recognition ligand). In studying the non-specific binding properties of the films in accordance with the present invention, waveguide-based sandwich assays have been used for the detection of a marker protein for *Bacillus anthracis* and direct comparisons have been made to results obtained using lipid bilayer membranes, the current best standard for minimizing non-specific binding.

In addition to creating biocompatible films with minimal non-specific binding, a low concentration of a reactive group at the terminus of the SAM molecules is included to permit conjugation of other chemical groups. This has been accomplished in a way that ensures that these additional chemical moieties are homogeneously dispersed throughout the remaining SAM. In effect, these additional chemical groups are surrounded by a sea of, e.g., methoxy terminated PEGs. In sensing, capturing, and scavenging applications this additional molecule m could be a recognition ligand that captures the target biomolecules. These recognition ligands could be antibodies, antibody fragments, aptamers, DNA, RNA, peptides, or carbohydrates. Alternately, for delivery of imaging agents (e.g., magnetic particles, radionuclides, optical nanoparticles, etc.) or drugs (e.g., porous silica beads with siRNA, any number of drugs such as Gleevec and the like) these SAMs could be functionalized with a number of tumor targeting (or diseased tissue targeting) molecules. Of course, for simple antifouling purposes, the homogeneous SAM with no additional chemical diversity would be used or needed.

The substrates in the present invention can generally be any material having an oxide surface, e.g., silicon dioxide, quartz, indium-tin oxide (ITO), aluminum zinc oxide (AZO) and other metal oxides. Further, the substrate could be a mesoporous silica material or could be a particle coated with a suitable mesoporous silica or metal oxide. For example, mesoporous silica or a suitable metal oxide could be coated onto a metal particle, a metal nanoparticle, a quantum dot or nanocrystal of a desired material. The particles that are coated could be magnetic or could yield other optical properties. A silica coating could be alternatively embedded with a suitable dye as well.

These substrates can be a surface in a sensing application, e.g., a surface of a waveguide device, of a SAW device, of a QCM device, of an interdigitated electrode for impendence based sensing. The substrates can be used in biomedical applications as well such as targeted drug delivery, medical diagnostics, imaging, e.g., cell imaging, and the like.

The waveguide architecture used with the present invention is described in detail by Kelly et al. in Optics Letters, vol. 24(23), pp. 1723-1724 (1999) such description incorporated herein by reference. A brief description of the waveguide is as follows. The waveguide consists of a high index of refraction, dielectric film sandwiched between a planar substrate and a coating, both with lower indices of refraction than the waveguiding material. Because of the difference in refractive index, the excitation laser light propagates along the high index material with approximately 120 reflections per millimeter, providing a strong interaction between the guided light and the surface. The intensity of the portion of light that extends beyond the sensor surface, called the evanescent field, decreases exponentially with distance from the surface. Therefore, the bulk solution volume is not irradiated while the field intensity at the SAM surface is still quite high. This is important for detecting small amounts of an analyte and for minimizing background fluorescence from solution.

For assays, the waveguide is fitted with a gasket and a coverslip to create a flow cell, and is placed in a sample cell holder in a test-bed laser spectrophotometer. The schematic of the test-bed system is shown in FIG. 1.

The assay used for testing the surfaces on waveguides was a sandwich assay based on detecting *Bacillus anthracis* protective antigen. In this assay, streptavidin bound to the biotinylated receptor surface (either membrane or SAM). In turn, a biotinylated capture antibody was added, followed by a fluorescently labeled detection antibody to determine the level of non-specific binding. The antigen was then added, followed by another aliquot of the detection antibody (FIG. 2). Rinsing with at least 10 aliquots of buffer followed each reagent addition.

Initially, phospholipid membranes were used as a sensing platform. Vesicles were prepared with the desired amount of biotinylated phospholipids (usually ≤1%) in DOPC and adsorbed onto the waveguide surface. The membrane imparted excellent resistance to non-specific binding and gave no background fluorescence (FIG. 3). However, membranes are very fragile. If a single air bubble is introduced into the flow cell, it disrupts the entire phospholipid bilayer. Additionally, in assays where non-specific binding was more of a problem, strong rinsing agents such as Tween-20 cannot be used because detergents will remove the bilayer. Finally, membranes do not offer binding flexibility in the types of analytes that can be examined. The use of membranes limits a researcher to receptors and ligands that are commercially available or readily prepared, effectively tying one to the typical biotin/avidin linkage. These issues led to examination of other surfaces that might survive a variety of handling, temperature, and rinsing conditions.

In analyzing the disadvantages of membranes, and comparing the goals for a robust sensor, prepared surfaces were sought that were stable to a variety of reagents and temperatures, readily prepared by known methods using commercially available reagents, flexible in the variety of functional groups that could be introduced, and would allow for a reusable sensor element. These attributes were desired in addition to maintaining the biological inertness of membranes. This led to the search for suitable SAMs for use in the present invention.

To address the above issues, modified self-assembled monolayer thin-films (SAMs) were designed and are shown in FIG. 4. These films were modeled after similar SAMs on gold and silver that were reported to resist non-specific adsorption of biomolecules due to the presence of poly-ethyleneglycol-terminated SAMs. Oxide or silica-based substrates had also been coated with this type of thin film, but not so specific binding or attachment of biological molecules was possible. The goal, therefore, was to prepare SAMs on oxide or silica surfaces that minimized non-specific absorption while allowing the specific attachment of molecules to a surface. Covalent attachment of PEGs to glass surfaces affords robustness, and with robustness comes the ability to rinse with detergents and more stringent rinsing agents, giving reusability.

Short alkyl chain SAMs were initially examined. Aminopropylsilane 1 was chosen due to its ease of use. SAMs using this silane were prepared using a known procedure. Reactive $PEG_6$-OH 3 was prepared and mixed with PEG amino acid 2 in a known ratio to afford surfaces 4. Fmoc-deprotection and coupling to biotin-OSu afforded surfaces 5 (FIG. 5).

Initial fluorescence microscopy initially showed positive results. Surfaces were prepared on glass or indium tin oxide in which a patterned region contained a small percentage of biotin (1-10% based on the ratios of 2 and 3 in solution) and the irradiated region contained only the surface that was more inert to biofouling (in this case, $PEG_6$-OH). The slides were immersed in FITC-streptavidin and rinsed with deionized water. Differentiation between regions where biotin was present and where it was absent could readily be accomplished. However, examination of these surfaces in a sandwich assay (see FIG. 2) showed that non-specific binding was a significant problem (FIG. 7a). Additional experiments in which only the reporter antibody was added showed that sequential additions led to increases in the signal due to non-specific binding (FIG. 7b).

The SAMs useful in the present invention were prepared from trifunctional alkyl, alkenyl or alkynyl silanes. Generally, the trifunctionality was trichloro, trimethoxy or triethoxy. The length of the chain is generally about 3 carbons or more. Examples of suitable silane materials include 1-bromoundecyltrichlorosilane, aminopropyldiethoxymethylsilane (APDEMS), aminoproyltriethoxysilane (APTES) and the like. For solution based preparation processes, longer chain silane materials such as 1-bromoundecyltrichlorosilane may be desired. For gas phase preparation processes, APDEMS and APTES may be desired with APDEMS allowing especially good results.

Later, the SAM surface can be functionalized by reaction with a mixture of species where one species provides a reactive site for attachment of a recognition element and the like and a second species serves to minimize non-specific binding. Generally, for sensing applications the ratio of the species addressing non-reactive binding will predominate and the ratio of that to the species providing the reactive site is from about 90:10 to about 99.9:0.1, more preferably from about 95:5 to about 99.9:0.1, and most preferably from about 99:1 to about 99.9:0.1.

These surfaces were problematic for several reasons. First, due to the difference in reactivity of the HOBt ester and the pNP ester, the actual surface composition was unknown, and was not reflected in the solution composition used to prepare the surfaces. Thus, the percentage of biotin on the surface was probably much higher than it would be if we had the same functionality on both PEG reagents. This problem did not become glaringly apparent until we tried to perform waveguide experiments with these films. Fluorescence microscopy showed excellent pattern definition because the non-specific binding was not as obvious through the microscope. Second, the solution grown aminopropyl silanes were very rough. This roughness gives rise to potential places for non-specific binding to occur. Blocking made a slight difference (See Tables 1 and 2), but not enough to avoid making some alterations to the process and/or the films.

TABLE 1

Selected SAM experiments[1] - Biotin percentage, Blocking

| Waveguide | % Biotin | BG[2] | NS[2] | S[2] | NS/BG | S/NS |
|---|---|---|---|---|---|---|
| RO22 | 3[3] | 313 | 2432 | 7500 | 7.8 | 3.1 |
|  | 0.5 | 137 | 2310 | 5350 | 16.5 | 2.3 |
| RO06 | 3 | 310 | 5000 | 2060 | 16.1 | 4.1 |
|  | 0.5 | 305 | 12690 | 32600 | 42.3 | 2.6 |

[1]the spectra represent photons counted over 3 seconds.
[2]BG = background, NS = non-specific binding, S = specific binding
[3]This SAM was blocked with 2% BSA for 2 hours

TABLE 2

Membrane Experiments[1] (presented for comparison)

| Waveguide | Block Agent | BG[2] | NS[2] | NS/BG |
|---|---|---|---|---|
| RO01 | 2% BSA | 71 | 90 | 1.3 |
|  |  | 142 | 149 | 1.0 |
| RO11 | 2% BSA | 250 | 250 | 1.0 |
|  |  | 227 | 212 | 0.9 |

Figure 8:
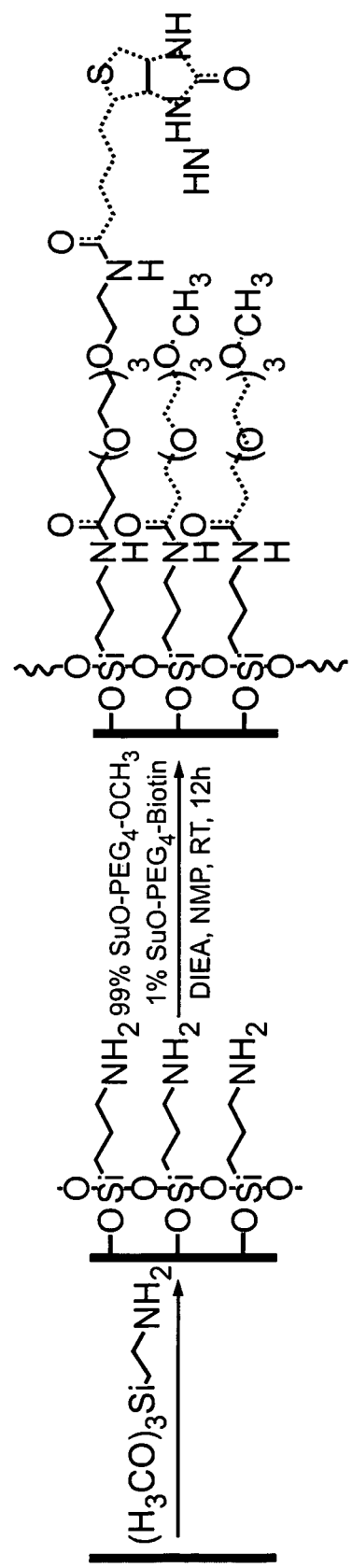
FIG. 8 shows preparation of modified short-alkyl chain SAMs using a vapor-phase process for silane deposition, such modified SAMs having only three carbons in the alkyl group and shown as a comparison to the materials of the present invention.

[1]the spectra represent photons counted over 3 seconds.
[2]BG = background, NS = non-specific binding Three changes were made. First, a vapor deposition method was employed in an attempt to avoid the issues tied to surface roughness. Atomic force microscopy showed that the vapor deposition method gave a SAM that avoided the nucleation growth of solution-phase methods, resulting in highly uniform surface coverage. With the increased uniformity and monolayer formation inherent in the vapor deposition method, trimethoxyalkanesilanes or trichloroalkanesilanes could be used as well as the diethoxysilanes. The third change involved locating to and purchasing PEG-reagents that were terminated with the same reactive functional group. The succinimide esters shown in FIG. 8 were typically used to prepare surfaces for waveguide assays, though other reagents are available that have protected amines rather than biotin, allowing for flexibility in the terminal functional group. In waveguide assays, these changes greatly reduced initial non-specific binding, but sequential additions of reporter antibody in the PA-waveguide assay continued to increase the level of non-specific binding.

SAM were sought that would give the stability and reusability of SAMs but would also have the anti-fouling properties of membranes. According to prior work by both Grosdemange et al. and Herrwerth et al. (previously cited above), a longer alkyl chain would allow for tighter packing of the SAM, leaving less space or flexibility for biological molecules to non-specifically bind. However, no commercially available aminoalkylsilanes met the desired needs for a starting surface. In one aspect of the present invention, a commercially available silane was modified after attaching it to a surface. This approach enhances surface flexibility for binding and decreases the difficulty of preparation and purification of sensor surfaces. This procedure required adding several steps to the surface preparation, but preparing an advanced intermediate that will allow higher throughput slide preparation and attachment of a variety of functional groups may also be appropriate.

Figure 9:
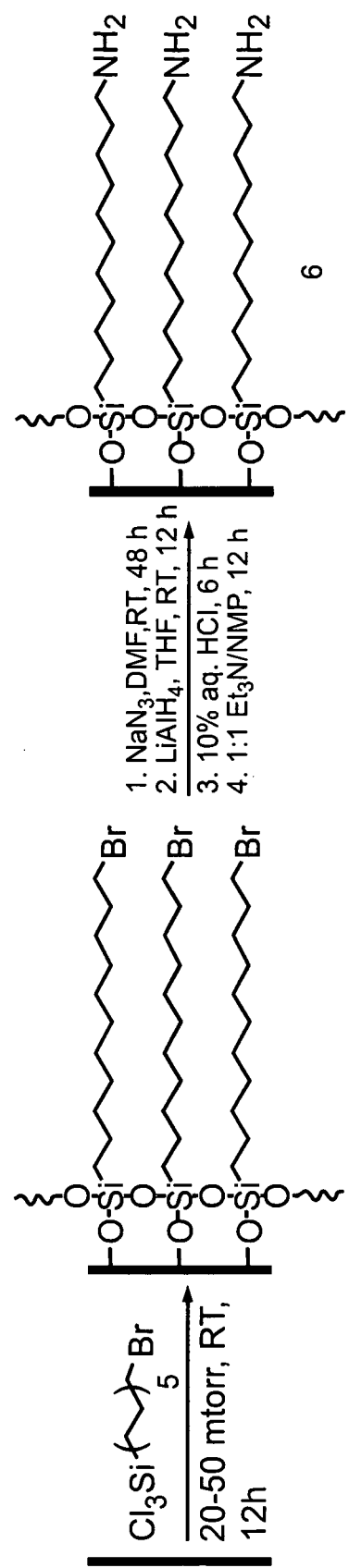
FIG. 9 shows preparation of an amine-terminated long-alkyl chain SAM used in accordance with the present invention.

Preparation of amine-terminated long-alkyl chain SAMs was carried out. To this end, 1-bromoundecyltrichlorosilane was attached to a glass surface either in solution or using a vapor deposition method. The vapor deposition was preferred because it gave more uniform monolayer coverage and did not require the use of solvent or heating. The terminal bromide was displaced by azide, and the azide was reduced by lithium aluminum hydride. The initial reduction product was immersed in dilute aqueous hydrochloric acid to quench the aluminates on the surface. Next, the slides were treated with 1:1 $Et_3$N/NMP to neutralize the hydrochloric acid salts of the terminal amines to afford surfaces 6 (FIG. 9).

Figure 10:
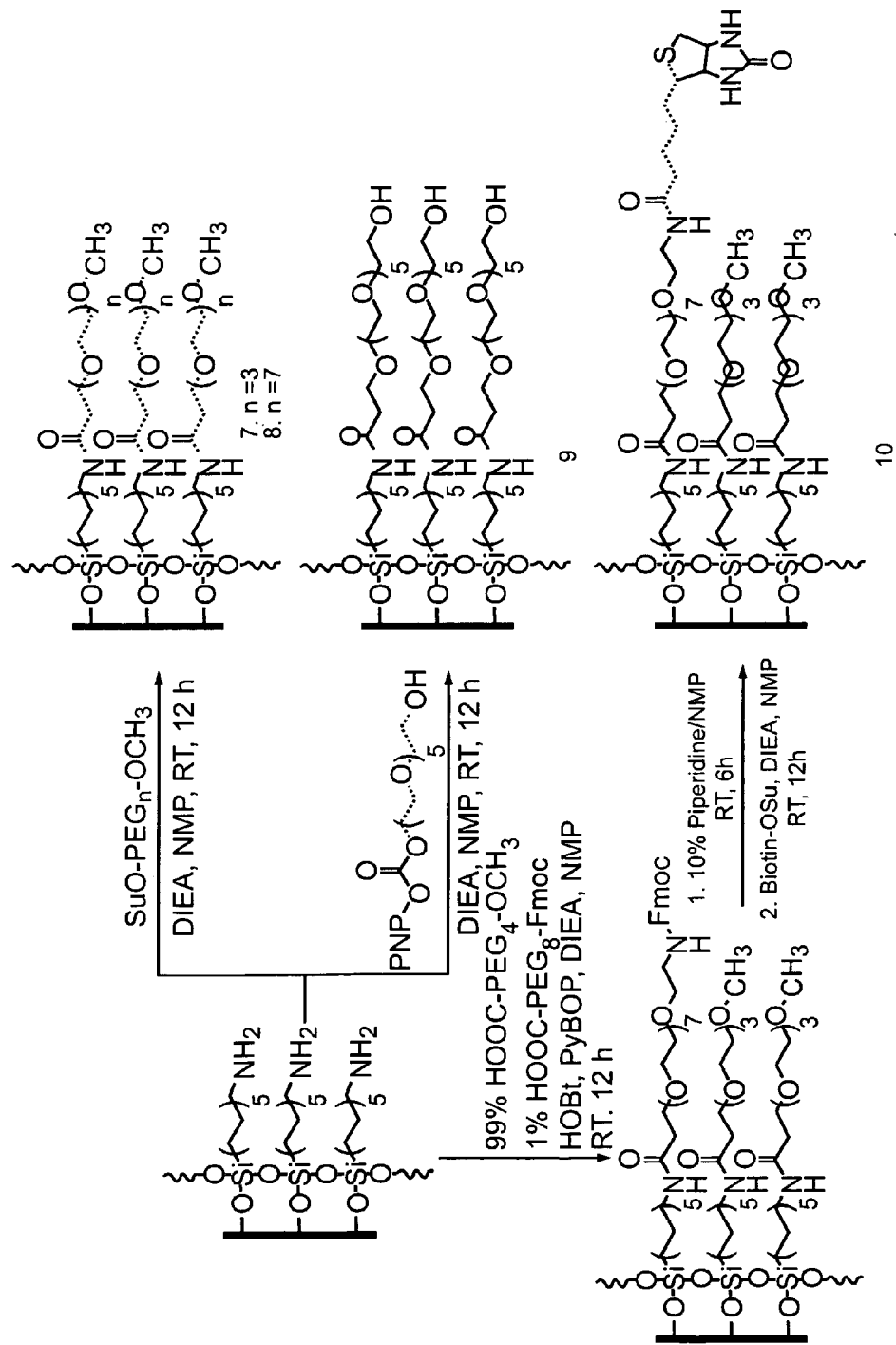
FIG. 10 shows preparation of other PEG-SAMs used in accordance with the present invention.

Surface 6 was modified using the chemistry shown in FIG. 10, path A. The resulting surfaces 7, 8, and 9 were used to test the resistance of these SAMs to non-specific binding. The surfaces were treated with sequential additions of reporter antibody then analyzed on the waveguide test-bed system to give the spectra shown in FIG. 11 A-C. A methoxy-terminated $PEG_8$ surface led to a significant increase in the non-specific binding signal with a second addition of reporter antibody, while methoxy-terminated PEG$_4$ and hydroxyl-terminated PEG$_6$ did not promote an increase. In fact, the signal due to non-specific binding on the PEG$_4$ surface actually decreased slightly. In light of these results, the PEG$_4$-OCH$_3$ surface doped with PEG$_8$-biotin was used for waveguide assays. The result is shown in FIG. 11D. These results are in good agreement with the prior work of both Grosdemange et al. and Herrwerth et al. on gold and silver surfaces.

The following results were observed.

Figure 1:
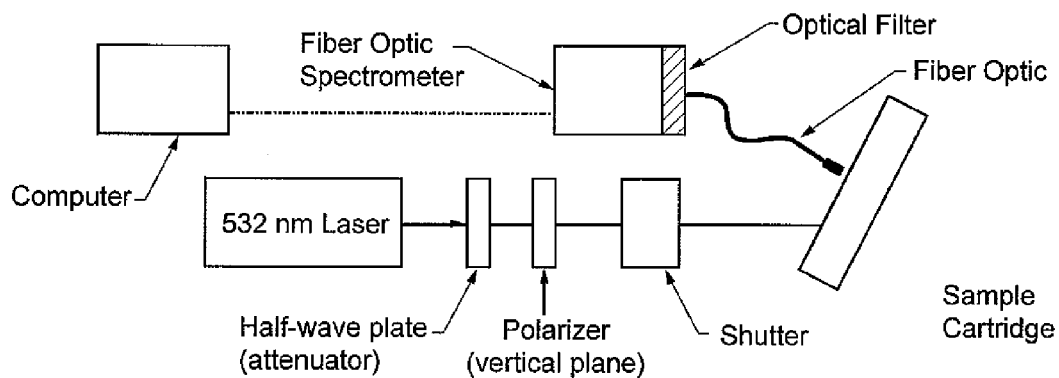
FIG. 1 illustrates a schematic drawing of a laser spectrophotometer/waveguide test bed system.

Solution Grown Long-Alkyl Chain SAMs:

Preparation of the present films requires either several modification steps on the surface or rigorous chemical synthesis of precursors. For ease of synthesis and flexibility of terminal groups, the method using modification steps on the surface can be chosen (FIG. 1), but preparation of PEG-SAM precursors may be necessary to decrease the turn-around time between runs.

To begin forming aminoalkylsilane surface 5, bromoundecyltrichlorosilane was reacted with an oxide surface to form the intermediate SAM. Analysis of the intermediate SAM by AFM showed that the surface coverage was quite rough, with tens of nanometers of surface roughness. While not wishing to be bound by the present explanation, the roughness is believed to be due to both uneven is coverage of the surface (some areas left bare) and the formation of mulitilayers. This may be a cause of non-specific binding in waveguide assays. Azide displacement of the bromide followed by lithium aluminum hydride reduction, aluminate quenching with 5% HCl, and deprotonation yielded surface 5. Ellipsometry of film 1 showed that the SAM was composed of from about 60-100% bromide/from about 0-40% methyl terminated alkyl chains. Contact angle supported the successful derivitization of the surface—SAM 1 yielded a contact angle of 82 degrees, azide displacement yielded 76 degrees, and reduction, quenching, and deprotonation yielded SAM 2 which gave a contact angle of 62 degrees. This value is nearly the same as the contact angle for the aminopropylsilanes used in earlier SAM work and agrees with literature values.

Figure 12:
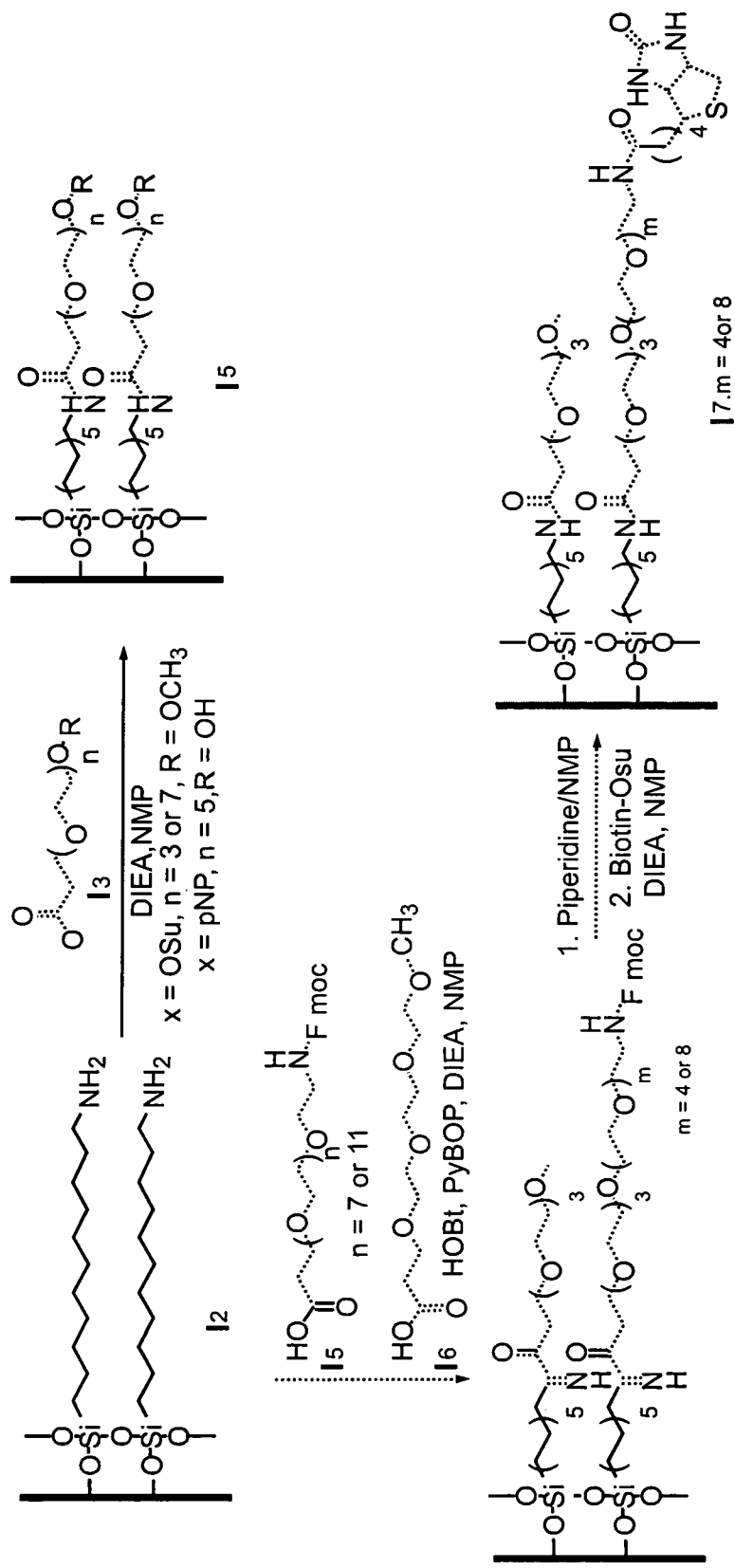
FIG. 12 shows modification of SAMs useful in accordance with the present invention.

Modification of 12 with PEG reagents 13 afforded surfaces 14, which were used in non-specific binding studies with these films. Alternatively, elaboration with PEG reagents 15 and 16, followed by deprotection and biotinylation could yield surface 17 (FIG. 12). Using PEG reagents 15 and 16 circumvents the problem with questionable biotin concentration on the surface because both reagents use the same method to attach to the amine surface.

The first waveguide experiments with modified-SAMs 14 proved promising. Reporter antibody was added, and the fluorescence intensity was measured. The emission due to non-specific binding was still high, but, in the case of PEG$_4$-OCH$_3$ and PEG$_6$-OH, did not increase with subsequent additions of reporter antibody. The next waveguide experiments utilized a 1% biotinylated SAM in a sea of PEG$_4$-OCH$_3$-terminated long alkyl chains to assess the surface in a binding assay. In these assays, the SAMs were blocked with 2% BSA, rinsed, and subjected to the sandwich assay.

Vapor Deposition:

Due to the success of both solution-grown long-alkyl chain SAMs and of aminopropysilane (APDEMS or APTES) vapor deposition, gas-phase growth of bromoundecylsilane films was examined. This route was successful as well, although longer reaction times were required than with aminopropylsilane due to the lower volatility of the larger silane. AFM analysis showed more uniform and even coverage than from solution deposition. This suggests that vapor deposition may be preferable in some instances. The results of waveguide-based sandwich assays performed using vapor-phase deposited SAMs continue to be good.

The vapor deposited SAMs were superior to the solution grown SAMs in minimizing non-specific binding. With use of APDEMS as the silane and using vapor deposition of the silane, a highly smooth level monolayer surface could be obtained.

Indeed the vapor deposited SAMs have been demonstrated to be nearly as good as lipid bilayer membranes (assays with membranes were conducted back-to-back with the assays using SAMs; see Table 1).

Patterning is not currently possibly because the azide reduction step is too harsh for amide bonds and PEG-ether bonds to survive. Survey and trial of milder reduction conditions using iodotrimethylsilane is currently underway.

The present invention has demonstrated that thin film materials can be developed that have optimal properties for biocompatibility for use in sensing, sample processing, antifouling and drug (or imaging) agent delivery. These films, and in particular vapor deposited films, exhibit outstanding properties in minimizing non-specific binding. Immediate applications include use in antifouling surfaces and as sensor surfaces. Although additional stability studies remain needed to test these films against exposure to high temperatures and complex fluids, such studies do not diminish the value of the present development.

For sensing applications, patterning of these SAMs on multi-element arrays will be important for multi-analyte sensing. These SAMs maintain low non-specific binding with dramatic increased stability compared to membranes and can therefore be deployed as reusable surfaces.

The present invention is more particularly described in the following examples which are intended as illustrative only, since numerous modifications and variations will be apparent to those skilled in the art.

Aminopropylmethyldiethoxysilane (APDEMS), aminopropyltriethoxysilane (APTES), and 11-bromoundecyltrichlorosilane were purchased from Gelest, Inc. Toluene, ethanol, acetone, hexadecane, N,N-diisopropylethylamine (DIEA), triethylamine, tetrahydrofuran (THE), N,N-dimethylformamide (DMF), lithium aluminum hydride (LAH, THF solution), 4-nitrophenylchloroformate, hexaethyleneglycol, piperidine, Fluorescein isothiocyanate (FITC)-streptavidin, and Tween-20 were purchased from Sigma-Aldrich, Inc. Tween-20 was diluted to 0.1% with 10 mM phosphate buffered saline (PBS) before use. N-Methylpyrrolidinone (NMP) and dichloromethane (CH$_2$Cl$_2$), both peptide synthesis grade, were purchased from Fisher. N-Hydroxybenzotriazole (HOBt), O-(benzotriazol-1-yl)-N,N,N',N'-tetramethyluronium hexafluorophosphate (HBTU), benzotriazol-1-yloxy) tripyrrolidino-phosphonium hexafluorophosphate (PyBOP), FmocNH-PEG$_{12}$-COOH, and Biotin succinimidyl ester (Blotin-OSu) were acquired from NovaBiochem/EMD Biosciense. H$_3$CO-PEG$_4$-COOH, H$_3$CO-PEG$_4$-OSu, H$_3$CO-PEG$_8$-OSu, FmocNH-PEG$_8$-COOH, and biotinyl-PEG$_4$-OSu were obtained from Quanta Biodesign. PBS was acquired from either Sigma-Aldrich or Gibco and diluted 10-fold before use. Neutravidin was purchased from Pierce Chemical, Rockford, Ill. Alexa-fluor 532 was acquired from Molecular Probes. FITC-streptavidin was purchased from either Pierce or Sigma. Triethylamine was filtered through silica gel before use to remove colored impurities. One-inch by three-inch glass microscope slides were acquired from Fisher. Waveguides were received from nGimat Co., Atlanta, Ga. The target for demonstration of these films in waveguide-based sandwich assays was protective antigen, a marker protein for *B. anthracis*, using antibodies (105 and 106) purchased from Tetracore, Inc., Rockville, Md. or Advanced ImmunoChemical, Inc., Long Beach, Calif.

New substrates were washed with ethanol and dried under a stream of argon or nitrogen. Previously used substrates (from membrane assay experiments) were sonicated for five minutes each in chloroform and ethanol and were blown dry. Silicon, glass, fused silica, and ITO slides were oxygen-plasma cleaned for 5 minutes on high power. Waveguides were UV-ozone cleaned for 30 minutes.

Example 1

Solution Phase Preparation of Aminopropylsilane Thin Films

Freshly cleaned slides were immersed in a solution of aminopropyl-diethoxymethylsilane (1% v/v) in toluene at room temperature. After 4 hours, these slides were removed, washed thoroughly with ethanol from a squirt bottle, and blown dry under a stream of argon, producing a film with an advancing water contact angle of 62±2 degrees above horizontal.

Example 2

Solution Phase Preparation of Bromoundecylsilane Thin Films

Freshly cleaned slides were immersed in a solution of bromoundecyl-trichlorosilane (3% v/v) in hexadecane or toluene. The reaction was heated to 60° C. for 4-6 hours then allowed to cool to room temperature. The slides were washed with $CH_2Cl_2$ and ethanol then blown dry under a stream of argon, producing a film with an advancing water contact angle of 82±2 degrees above horizontal.

Example 3

Gas-Phase Preparation (Vapor Deposition) of Aminopropylsilane (Triethoxy and Diethoxymethyl) Thin-Films Substrates were cleaned using UV-ozone, oxygen plasma, or sulfuric acid/hydrogen peroxide (piranha cleaning). The freshly cleaned substrates were rinsed with water, blown dry, and placed in a glass Petri dish with a small sample of the appropriate silane (50 µl) in a watch glass. The cover was placed on the top of the Petri dish, and the entire dish was placed in a vacuum desiccator. The desiccator was evacuated to about 60 kPa (about 140 torr) and held at static vacuum for 2 hours. The silane sample was discarded, and the substrates were placed in a drying oven at 100-120° C. for 1 hour. The substrates were allowed to cool in a drying desiccator, and were washed with ethanol and blown dry under a stream of argon. Water contact angle: 54-64° for both di- and tri-ethoxy silane SAMs.

Example 4

Gas Phase Preparation (Vapor Deposition) of 11-Bromoundecyltrichlorosilane Thin Films Substrates were cleaned using UV-ozone, oxygen plasma, or sulfuric acid/hydrogen peroxide (piranha cleaning). The freshly cleaned substrates were placed in a glass Petri dish with a small sample of 11-bromoundecyltrichlorosilane (50 µl). The cover was placed on the top of the Petri dish, and the entire dish was placed in a vacuum desiccator. The desiccator was evacuated to 200 mtorr and kept under active vacuum overnight. The silane sample was discarded, and the substrates were placed in a drying oven at 100-120° C. for 1 hour. The substrates were allowed to cool in a drying desiccator, and were washed with ethanol and blown dry under a stream of argon. Water contact angle: 82-88°.

Example 5

Bromide Displacement

Slides coated with covalently attached bromoundecylsilane were immersed in saturated $NaN_3$/DMF and shaken vigorously for 2 days. The slides were washed with NMP, $CH_2Cl_2$, and EtOH (alternatively acetone, water and ethanol) then blown dry under a stream of argon, producing a film with an advancing water contact angle of 76±1 degrees above horizontal.

Example 6

Azide Reduction

Azide-coated slides were reduced in two ways, depending on whether or not patterning was necessary. In the first method, the slides were immersed in dry THF under argon and $LiAlH_4$ was added. This reaction was shaken vigorously overnight. The slides were washed with ethanol and water and immersed in 0.5 M HCl for 4 hours. The slides were washed with water, acetone and NMP (or ethanol) and immersed in 1:1 $Et_3$N/NMP (to neutralize the resulting HCl salt and provide the surface amine) and then the slides were washed with NMP (or $CH_2Cl_2$), acetone and ethanol and blown dry under a stream of argon. These steps produced the amine-terminated long-alkyl chain SAMs with an advancing water contact angle of 62±3 degrees above horizontal.

In the second method, sodium iodide was dissolved in acetonitrile, and chlorotrimethylsilane (TMS-Cl) was added drop-wise. The resulting solution was allowed to stir for 5 minutes, during which time it turned from clear and colorless to pale gray and cloudy to clear. This solution was cannulated into a jar or flask containing the substrates in acetonitrile. After 2 hours, the reaction turned yellow. The slides were washed with acetonitrile and water and submerged in 10% aqueous $Na_2S_2O_3$ overnight. The slides were washed with water and ethanol and blown dry under a stream of argon, producing a film with an advancing water contact angle of 60±3 degrees above horizontal.

Example 7

Attachment of PEG-Carboxylic Acids

FmocNH—$CH_2CH_2$-$PEG_x$-COON (x=4, 8, 12; 0.001-0.1 mM) was mixed with $H_3$CO-$PEG_4$-COOH (0.9-0.999 mM) so the total concentration of PEG reagents was 1 mM. This PEG mixture was added to a solution of PyBOP (0.95 mM), and DIEA (2 mM) in NMP (5-10 ml). The reaction mixture was allowed to stand 15-30 minutes, and was diluted to the appropriate reaction volume and poured over the substrates. After shaking vigorously overnight, the slides were washed with NMP, acetone, and ethanol and were blown dry under a stream of argon prior to analysis. Water contact angle: 42-48 for 0.1-1% FmocNH-PEG slides.

Example 8

Attachment of Biotinyl- and PEG-Succinimide Esters

PEG films that contained Fmoc-amine terminated PEGs were treated with 10% piperidine/NMP for 6-8 hours. The slides were washed thoroughly with NMP, $CH_2Cl_2$ and EtOH, and blown dry under a stream of argon. The slides were treated with the appropriate succinimide ester ($CH_3O$-$PEG_4$-OSu, $CH_3O$-$PEG_8$-OSu, or Biotin-OSu (1 mM)) and DIEA (2 mM)) in NMP (50 ml) for 10-12 hours at room temperature. The slides were washed with NMP, $CH_2Cl_2$ and EtOH and were blown dry under a stream of argon. Note that the contact angle does not change between Fmoc removal and biotinylation because the percentage of reactive groups is low.

Example 9

Patterning for Fluorescence Microscopy

Thin films on glass that contained biotin were patterned using a photomask (chrome pattern on fused silica) and UV-ozone irradiation. The areas where the SAM was removed were filled in by attaching the aminopropylsilane and attaching the appropriate PEG reagent (see Example 7) (or attaching a PEGylated undecyltrichlorosilane). These patterned slides were used in fluorescence microscopy assays.

Fluorescence Microscopy Assays:

A patterned slide was immersed in a 1× (~0.01 M) PBS solution of FITC-streptavidin (0.4-4 µg/ml) for 1-2 minutes. The slide was immersed in 1×PBS, shaken, and washed with deionized water from a squirt/squeeze bottle. The slide was blown dry and analyzed by fluorescence microscopy.

Waveguide Assays:

Waveguides were cleaned and functionalized as described above, and were fitted with a silicon rubber gasket and a ported coverslip. This assembly was placed in a plastic flow cell and placed in our test-bed system (see FIG. 2) to analyze the detection of *B. anthracis* protective antigen (PA). The flow cell was filled with 0.5% BSA/1×PBS and the waveguide background fluorescence was recorded. Neutravidin and biotinylated-105 α-PA were added, and another background spectrum was taken. Typically, no change in fluorescence intensity occurred after the addition of the capture reagents. An aliquot of Alexa-Fluor532-labeled-106 α-PA was added, and another spectrum was obtained to measure non-specific binding. After addition of PA and another aliquot of labeled 106, a final spectrum was taken to measure specific binding. The ratios of non-specific binding to background (NSB/BG) and specific binding to non-specific binding (SB/NSB) were calculated to allow comparison between waveguides. Between steps, the waveguides were rinsed with 10-20 flow cell volumes (1.5-3 ml) of 0.1% Tween-20 detergent in 1×PBS.

Figure 13:
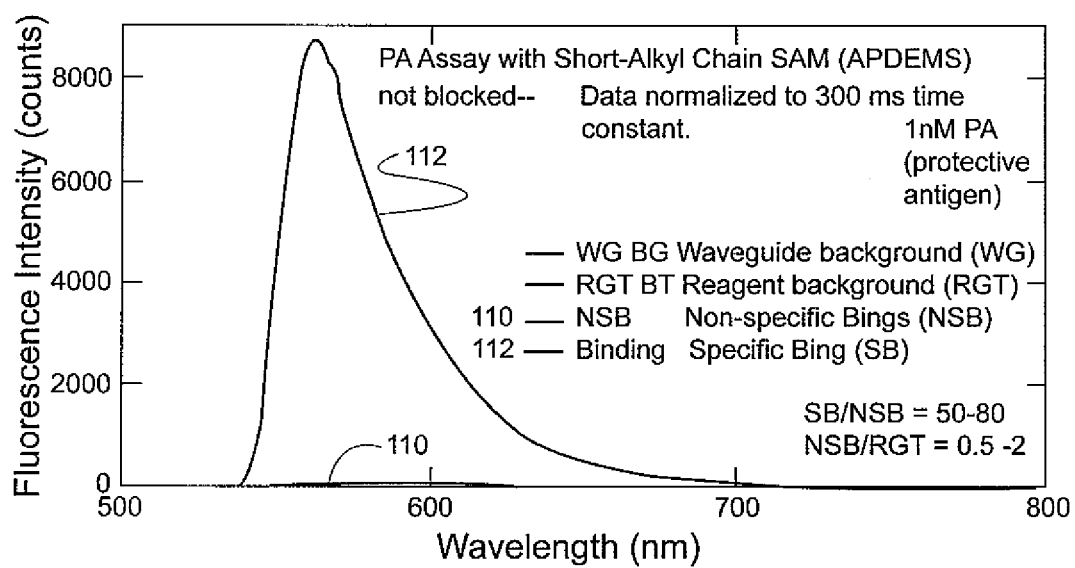
FIG. 13 shows a graph of a waveguide assay for 1 nM of PA (protective antigen) with a SAM from the silane, APDEMS, also with a PEG4-OCH3 group, as the terminal end for reduced non-specific binding. The graph shows the binding and the low level of non-specific binding showing a ratio of non-specific binding to background of from about 0.5 to 2 and a ratio of specific binding to non-specific binding of 50-80.
Figure 14:
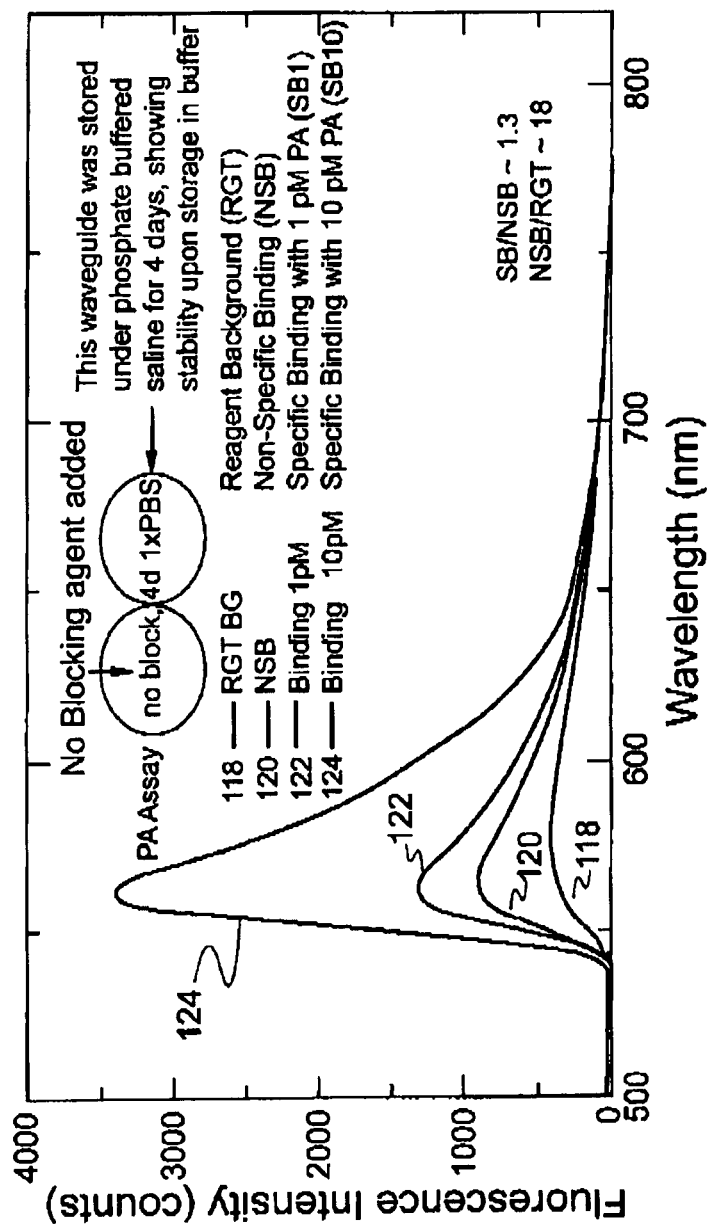
FIG. 14 shows a graph of a waveguide assay for 1 picoM (pM) and 10 pM of PA with a SAM from the silane, APDEMS, also with a PEG4-OCH3 group, as the terminal end for reduced non-specific binding. The graph shows the binding with both the 1 pM and 10 pM PA concentrations as well as the low level of non-specific binding. A ratio specific binding to non-specific binding of about 1.3 is shown for the detection of the 1 pM PA and of about 18 for the detection of the 10 pM PA.

The results shown in FIGS. 13 and 14 demonstrate the ability to detect low levels of a target species, but with low non-specific binding levels, using the present invention. Detection with low levels of non-specific binding was also achieved during an assay of a PA-spiked sample of Bovine Growth Serum.

Although the present invention has been described with reference to is specific details, it is not intended that such details should be regarded as limitations upon the scope of the invention, except as and to the extent that they are included in the accompanying claims.

What is claimed is:

1. A method of detecting a target species comprising:
providing a substrate having an oxide surface;
reacting a suitable silane material with the oxide surface by vapor phase deposition to deposit a monolayer on said oxide surface, the monolayer including a first species of the formula X-Q-$Z_1$ where X includes a silicon atom from a trifunctional alkyl/alkenyl/alkynyl silane group for attachment to the oxide surface, Q represents a central portion of the trifunctional alkyl/alkenyl/alkynyl silane group and serves as a spacer group of an alkane, or a combination of an alkane and one or more of an alkene or an alkyne group having greater than about 3 carbons, the spacer group promoting self-assembly of a plurality of said species, and $Z_1$ is a functional moiety that provides a site for attachment of a recognition ligand (R) adapted for binding to a pre-selected target species, and, a second species of the formula X-Q-$Z_2$ where X includes a silicon atom from a trifunctional alkyl/alkenyl/alkynyl silane group for attachment to the oxide surface, Q represents a central portion of the trifunctional alkyl/alkenyl/alkynyl silane group and serves as a spacer group of an alkane, or a combination of an alkane and one or more of an alkene or an alkyne group having greater than about 3 carbons, the spacer group promoting self assembly of a plurality of said species, $Z_2$ is a functional moiety that provides a site for attachment of a terminal moiety (T) that provides resistance to non-specific binding upon the sensor element;
conjugating the recognition ligand (R) to $Z_1$;
contacting a sample including a potential target species with the monolayer; and
detecting a signal arising in response to binding between said recognition ligand and any said pre-selected targeted species.

2. The method of claim 1 wherein all of the spacer groups have the same length of carbon atoms.

3. The method of claim 1 wherein the spacer groups are alkane groups each having the same length of carbon atoms.

4. The method of claim 1 further including a polyalkylene glycol spacer group having from about 3 to 7 repeating units between both functional moiety $Z_1$ and the recognition ligand (R) and functional moiety group $Z_2$ and the terminal moiety (T) that is resistant to non-specific binding.

5. The method of claim 4 wherein said polyalkylene glycol is polyethylene glycol.

6. The method of claim 1 wherein said substrate surface has defined portions of the surface including only a monolayer thereon said oxide surface of said second species of the formula X-Q-$Z_2$ where X includes a silicon atom from a trifunctional alkyl/alkenyl/alkynyl silane group for attachment to the oxide surface, Q represents a central portion of the trifunctional alkyl/alkenyl/alkynyl silane group and serves as a spacer group of an alkane, or a combination of an alkane and one or more of an alkene or an alkyne group having greater than about 3 carbons, the spacer group promoting self-assembly of a plurality of said species, and $Z_2$ is a functional moiety that provides a site for attachment of a terminal moiety (T) that provides resistance to non-specific binding by the composite material.

7. The method of claim 1 wherein said substrate is selected from the group consisting of silicon dioxide, quartz, indium-tin oxide (ITO) and aluminum zinc oxide (AZO), mesoporous silica particles, metal oxide coated metal nanoparticles, metal oxide coated metal particles and metal oxide coated glass particles.

8. The method of claim 7 wherein said substrate is silicon dioxide, Q is a —$(CH_2)_3$— group, $Z_1$ is a —NH— group, T is a methoxy group or a hydroxy group and R is a biotin group, an iodomethyl carbonyl group or a carboxymethyl-2-oxoethyl ether group.

9. The method of claim 7 wherein said substrate is silicon dioxide, Q is a —$(CH_2)_{11}$— group, $Z_1$ is a —NH— group, T is a methoxy group or a hydroxy group and R is a biotin group, an iodomethyl carbonyl group or a carboxymethyl-2-oxoethyl ether group.

10. A method of detecting a target species comprising:
a) providing a cleaned substrate comprising an oxide surface;
b) depositing a monolayer of species X-Q onto the substrate by vapor deposition comprising a reaction with a suitable silane, where X includes a silicon atom from a trifunctional alkyl/alkenyl/alkynyl silane group for attachment to the oxide surface and Q represents a central portion of the trifunctional alkyl/alkenyl/alkynyl silane group and serves as a spacer group of an alkane, or a combination of an alkane and one or more of an alkene or an alkyne group having greater than about 3 carbons, the spacer group promoting self-assembly of a plurality of said species;
c) attaching to Q one of a functional moiety $Z_1$ or $Z_2$, where $Z_1$ is a functional moiety that provides a site for attachment of a recognition ligand (R) adapted for binding to a pre-selected target species, and $Z_2$ is a functional moiety that provides a site for attachment of a terminal moiety (T) that provides resistance to non-specific binding upon the sensor element; and,
d) detecting a signal arising in response to binding between said recognition ligand and any said pre-selected targeted species.

11. The method of claim 10 wherein all of the spacer groups have the same length of carbon atoms.

12. The method of claim 10 wherein the spacer groups are alkane groups each having the same length of carbon atoms.

13. The method of claim 10 further including a polyalkylene glycol spacer group having from about 3 to 7 repeating units between both functional moiety $Z_1$ and the recognition ligand (R) and functional moiety group $Z_2$ and the terminal moiety (T) that is resistant to non-specific binding.

14. The method of claim 10 wherein said polyalkylene glycol is polyethylene glycol.

15. The method of claim 10 wherein said substrate surface has defined portions of the surface including only a monolayer thereon said oxide surface of said second species of the formula X-Q-$Z_2$ where X includes a silicon atom from a trifunctional alkyl/alkenyl/alkynyl silane group for attachment to the oxide surface, Q represents a central portion of the trifunctional alkyl/alkenyl/alkynyl silane group and serves as a spacer group of an alkane, or a combination of an alkane and one or more of an alkene or an alkyne group having greater than about 3 carbons, the spacer group promoting self-assembly of a plurality of said species, and $Z_2$ is a functional moiety that provides a site for attachment of a terminal moiety (T) that provides resistance to non-specific binding by the composite material.

16. The method of claim 10 wherein said substrate is selected from the group consisting of silicon dioxide, quartz, indium-tin oxide (ITO) and aluminum zinc oxide (AZO), mesoporous silica particles, metal oxide coated metal nanoparticles, metal oxide coated metal particles and metal oxide coated glass particles.

17. The method of claim 16 wherein said substrate is silicon dioxide, Q is a —$(CH_2)_3$— group, $Z_1$ is a —NH— group, T is a methoxy group or a hydroxy group and R is a biotin group, an iodomethyl carbonyl group or a carboxymethyl-2-oxoethyl ether group.

18. The method of claim 16 wherein said substrate is silicon dioxide, Q is a —$(CH_2)_{11}$— group, $Z_1$ is a —NH— group, T is a methoxy group or a hydroxy group and R is a biotin group, an iodomethyl carbonyl group or a carboxymethyl-2-oxoethyl ether group.

* * * * *